United States Patent [19]
Powell

[11] 3,985,735
[45] Oct. 12, 1976

[54] PYRIMIDO(4,3-b)(1,3)THIAZIN-6-ONES
[75] Inventor: James E. Powell, Modesto, Calif.
[73] Assignee: Shell Oil Company, Houston, Tex.
[22] Filed: June 30, 1975
[21] Appl. No.: 591,738

[52] U.S. Cl. .................... 260/243 R; 260/240 R; 424/246
[51] Int. Cl.$^2$ .................................. C07D 279/08
[58] Field of Search.......... 260/243 R, 240 R, 240 F

[56] References Cited
OTHER PUBLICATIONS

Hirai et al., *Chem. Pharm. Bull*, vol. 20, pp. 97–101 (1972).

*Primary Examiner*—John M. Ford

[57] ABSTRACT

Novel insecticidal 3,4,7,8-tetrahydro-9-nitro-2H,6H-pyrimido(4,3,b)(1,3)thiazin-6-ones. b)(1,3)thiazin-6-ones.

3 Claims, No Drawings

PYRIMIDO(4,3-B)(1,3)THIAZIN-6-ONES

DESCRIPTION OF THE INVENTION

It has been found that useful insecticidal activity is possessed by certain 3,4,7,8-tetrahydro-9-nitro-2H,6H-pyrimido(4,3-b) (1,3)thiazin-6-ones of the formula

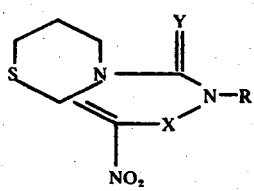

wherein Y is oxygen or sulfur, R contains up to twenty carbon atoms and is (a) straight-chain or branched-chain alkyl or alkenyl; or (b) cycloalkyl, phenyl, phenalkyl, phenylcycloalkyl, or these substituted by one or more of halogen, straight-chain or branched-chain alkyl or alkoxy of from one to six carbon atoms, nitro or cyano; and X is

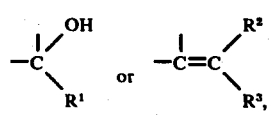

wherein $R^1$ is hydrogen; phenyl or phenyl substituted as indicated above; vinyl, mono- or polyhalovinyl; ethinyl or 2-phenylethinyl, optionally substituted on the ring as indicated above; or is

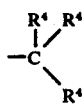

wherein each of $R^4$ independently is alkyl, halogen or phenyl optionally substituted as indicated above, $R^2$ and $R^3$ each is hydrogen, straight-chain or branched-chain alkyl of from 1 to ten carbon atoms, phenyl or phenyl substituted as indicated above.

Because of their insecticidal activity characteristics, one preferred sub-class of the compounds of this invention consists of those compounds wherein Y is oxygen, R is alkyl of from one to four carbon atoms, and X is

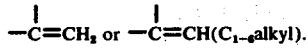

For similar reasons, another preferred subclass consists of those compounds wherein Y is oxygen, R is alkyl of from one to four carbon atoms and X is

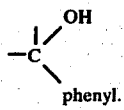

For illustration, preparation of typical species of the genus is described in the examples included hereinafter. Other typical, illustrative species of this genus include those wherein the symbols represent the following moieties, this manner of naming these species being accurate, yet pointing out the differences between the different species more clearly than if the entire, complicated name of each species were to be given:

| Y | R | X |
|---|---|---|
| S | methyl | $-\overset{|}{C}=CH_2$ |
| S | cyclopropyl | $-\overset{|}{C}=CHCH_2CH_3$ |
| S | methyl | $-\overset{|}{C}\overset{phenyl}{\diagdown}_{OH}$ |
| O | methyl | $-\overset{|}{C}\overset{vinyl}{\diagdown}_{OH}$ |
| S | methyl | $-\overset{|}{C}=CH_2$ |
| O | phenyl | $-\overset{|}{C}=CH_2$ |
| O | phenyl | $-\overset{|}{C}\overset{phenyl}{\diagdown}_{OH}$ |
| O | allyl | $-\overset{|}{C}=CH_2$ |
| O | butyl | $-\overset{|}{C}=CH_2$ |
| O | cyclohexyl | $-\overset{|}{C}\overset{tert\text{-}butyl}{\diagdown}_{OH}$ |
| O | butyl | $-\overset{|}{C}\overset{(ethinyl)}{\diagdown}_{OH}$ |
| O | methyl | $-\overset{|}{C}=C\overset{H}{\diagdown}_{phenyl}$ |

Compounds of this invention can be prepared by treating a ketone of the formula

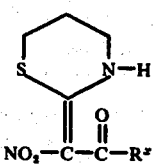

with an R-isocyanate (Y is O) or R-isothiocyanate (Y is S), wherein $R^x$ is $R^1$ or

Where $R^x$ contains an alpha hydrogen atom, the reaction can proceed with loss of water, involving that hydrogen atom, the hydrogen atom on the ring nitrogen atom of the ketone and the oxygen of the ketone, to form the subclass wherein X is

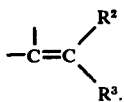

Where $R^x$ does not contain an alpha hydrogen atom, as with the phenyl ketones ($R^x$ is $R^1$) then the hydrogen atom on the ring nitrogen atom of the ketone reacts with the oxygen atom of the ketone to form hydroxyl, X being

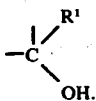

The ketone precursors are the subject of application Ser. No. 514,417 issued on June 8, 1976, as U.S. Pat. No. 3,962,225. For the purpose of describing preparation of said precursors, the pertinent portions of said application are incorporated herein.

Reaction of the ketone and iso(thio)cyanate is conveniently effected by heating a mixture of the ketone and a stoichiometric excess of the iso(thio)cyanate in an inert solvent and in the presence of a small amount of a tertiary amine to a moderately elevated temperature. Tetrahydrofuran is a suitable solvent; conducting the reaction at the reflux temperature of the mixture is a convenient technique. Triethylamine is a suitable tertiary amine. The desired product can be removed from the reaction mixture by conventional techniques. In some cases, it may be recovered simply by stripping volatile materials, including the solvent, from the crude reaction mixture. In other cases, the crude reaction mixture can be treated with an alcohol, such as isopropyl alcohol, which precipitates the crude product, which can be recovered by decantation and/or filtration techniques. The crude product can be purified by recrystallization and/or elution (chromatographic) techniques.

These procedures for preparing compounds of this invention are illustrated in the following examples of the preparation of particular species of such compounds. In all cases the identity of the thiazine precursor was established and the identity of the final product was confirmed by elemental analysis and by infrared and nuclear magnetic resonance spectrum analyses:

EXAMPLE 1 —
3,4,7,8-tetrahydro-7-methyl-8-methylene-9-nitro-2H,6H-pyrimido(4,3-b) (1,3)thiazin-6-one (1)

3.0 g of methyl isocyanate was added dropwise at 22° to a mixture of 10.1 g of 1-nitro-1-(tetrahydro-2H-1,3-thiazin-2-ylidene)-2-propanone, prepared as described in Example 2 of Ser. No. 514,417, in 75 ml of tetrahydrofuran, containing 0.25 ml of triethylamine, under nitrogen. The mixture was stirred for 3 hours at 22°–25°, then refluxed for 12 hours. An additional 3.0 g of methyl isocyanate was added and the mixture was refluxed 12 hours, then 15.0 g more of methyl isocyanate was added in 3.0 g portions to the refluxing mixture over a period of 30 hours, after which the mixture was refluxed for 4 hours and diluted with isopropyl alcohol. The solid product that formed was collected, washed with isopropyl alcohol and ether to give 1, as a rust colored powder, m.p.: 126.5°–128.5°.

EXAMPLE 2 —
3,4,7,8,-tetrahydro-7-methyl-9-nitro-8-propylidene-2H,6H-pyrimido(4,3-b) (1,3)thiazin-6-one (2)

6.9 g of 1-nitro-1-(tetrahydro-2H-1,3-thiazin-2-ylidene)-2-pentanone, prepared as described in Example 5 of Ser. No. 514,417, in 110 ml of tetrahydrofuran containing 0.25 ml of triethylamine, was treated by the procedure described in Example 1 with 40 ml of methyl isocyanate, in 10 ml portions, total refluxing time being 47 hours. The volatile materials then were stripped from the reaction mixture to give a light orange solid. Recrystallization from ether gave 2, as a bright orange solid, m.p.: 155°–156°.

EXAMPLE 3 —
3,4,7,8-tetrahydro-8-hydroxy-7-methyl-9-nitro-8-phenyl-2H,6H-pyrimido(4,3-b) (1,3)-thiazin-6-one (3)

A mixture of 6.6 g of 2-nitro-1-phenyl-2-(tetrahydro-2H-1,3-thiazin-2-ylidene)ethanone, prepared as described in Example 1 of Ser. No. 514,417, 50 ml of tetrahydrofuran, 0.25 ml of triethylamine and 10 ml of methyl isocyanate was refluxed for 5 hours. 10 ml of methyl isocyanate was added and refluxing continued for 1.5 hours, when 30 ml of tetrahydrofuran was added and the mixture was stirred at room temperature for 16 hours. The solvent then was evaporated under reduced pressure to leave a caramel-colored semisolid. The product was crystallized from ethyl acetate and ether to give a bright yellow solid, which was recrystallized from methylene chloride and ether twice to give 3, as a bright yellow solid, m.p.: 155°–156°.

Compounds of this invention exhibit useful insecticidal activity, being of particular interest for control of the larval "caterpillar" or "worm" forms of insects of the genus Heliothis, such as *H. Zea* (corn earworm, cotton bollworm, tomato fruitworm), *H. virescens* (tobacco budworm); the genus Agrotis, such as *A. ipsilon* (black cutworm); the genus Trichoplusia, such as *T. ni* (cabbage looper), and the genus Spodoptera, such as *S. littoralis* (Egyptian cotton leafworm). In tests that have been conducted they have exhibited low, or no, toxicity to other insects such as houseflies, pea aphids, 2-spotted spider mites and mosquito larvae. Activity with respect to mosquito larvae was determined by placing the larvae in water containing the test compound.

Activity of compounds of this invention with respect to insects was determined by using standardized tests to establish the $LC_{50}$ dosage (in milligrams of test compound per 100 milliliters of solvent or liquid carrier required in the solution or suspension of test compound used) that was required to kill 50% of the test insects. The test insects were the housefly, corn earworm, mosquito, pea aphid and 2-spotted spider mite.

All of compounds 1, 2 and 3 were found to be inactive or but slightly active with respect to the flies, aphids, mites and mosquito larvae. With respect to the corn earworm, all of the compounds were found to be active.

In the course of these tests it was noted that compound 1 acted very quickly upon corn earworms.

The invention includes within its scope insecticidal compositions comprising an adjuvant -- that is, a carrier, optionally a surface-active agent -- and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as for example, coumarone resins, polyvinyl chloride and styrene polymers and copolymers, solid polychlorophenols; bitumen, waxes such as beeswax, paraffin wax and chlorinated mineral waxes; degradable organic solids such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons, such as benzene, toluene and xylene; petroleum fractions, such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3-10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0-10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e., the dosage to which the insect contacts — is of the order of 0.001% to 0.5% based on the total weight of the formulation, though under some circumstances

What is claimed is:

1. A compound of the formula

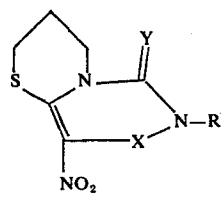

wherein Y is oxygen or sulfur, R contains up to 20 carbon atoms and is (a) straight-chain or branched-chain alkyl or alkenyl; or (b) cycloalkyl, phenyl, phenalkyl, phenylcycloalkyl, or these substituted by one or more of halogen, straight-chain or branched-chain alkyl or alkoxy of from one to six carbon atoms, nitro or cyano; and X is

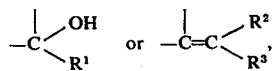

wherein $R^1$ is hydrogen; phenyl or phenyl substituted as indicated above; vinyl, mono- or polyhalovinyl; ethinyl or 2-phenylethinyl, optionally substituted on the ring as indicated above; or is

wherein each of $R^4$ independently is methyl, halogen or phenyl optionally substituted as indicated above; $R^2$ and $R^3$ each is hydrogen, straight-chain or branched-chain alkyl of from 1 to ten carbon atoms, phenyl or phenyl substituted as indicated above.

2. A compound according to claim 1 wherein Y is oxygen, R is alkyl of 1 to 4 carbon atoms and X is

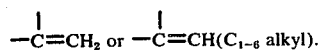

3. A compound according to claim 1 wherein Y is oxygen, R is alkyl of 1 to 4 carbon atoms and X is

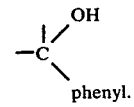

* * * * *